United States Patent
Singla et al.

(10) Patent No.: US 10,918,371 B2
(45) Date of Patent: Feb. 16, 2021

(54) APPARATUS AND METHOD FOR RETRACTING BRAIN TISSUE DURING BRAIN SURGERY

(71) Applicant: BRAIN INNOVATIONS LLC, Bellevue, WA (US)

(72) Inventors: Amit Singla, Bellevue, WA (US); Michael David Allen, Rochester, NY (US)

(73) Assignee: BRAIN INNOVATIONS LLC, Bellevue, WA (US)

( * ) Notice: Subject to any disclaimer, the term of this patent is extended or adjusted under 35 U.S.C. 154(b) by 0 days.

(21) Appl. No.: 16/373,888

(22) Filed: Apr. 3, 2019

(65) Prior Publication Data

US 2020/0315604 A1    Oct. 8, 2020

(51) Int. Cl.
*A61B 17/02*  (2006.01)
*A61B 90/00*  (2016.01)

(52) U.S. Cl.
CPC ...... *A61B 17/0293* (2013.01); *A61B 17/0206* (2013.01); *A61B 2090/0817* (2016.02)

(58) Field of Classification Search
CPC ............ A61B 17/1285; A61B 17/6441; A61B 17/0218; A61B 17/0293; A61B 17/0281; A61B 17/025; A61B 17/02; A61B 17/0206; A61B 2017/0212
See application file for complete search history.

(56) References Cited

U.S. PATENT DOCUMENTS

| 4,239,036 A | 12/1980 | Krieger |
| 4,457,300 A | 7/1984 | Budde |
| 4,510,926 A | 4/1985 | Inaba |

(Continued)

FOREIGN PATENT DOCUMENTS

| CN | 205234548 U | 5/2016 |
| CN | 206120374 U | 4/2017 |

(Continued)

OTHER PUBLICATIONS

Rachid Assina et al., Neurosurgical FOCUS, The history of brain retractors throughout the development of neurological surgery, Apr. 2014, DOI: 10.3171/2014.2.FOCUS13564 • Source: PubMed.

*Primary Examiner* — Matthew J Lawson
(74) *Attorney, Agent, or Firm* — Timothy E. Siegel Patent Law, PLLC; Timothy E. Siegel

(57) ABSTRACT

An assembly for facilitating brain surgery performed through an opening having a rim, created in the skull of a patient and having a curved frame, defining an inward dimension and an outward dimension. Also, at least one clamp arm subassembly is attached to the frame, and has a clamp arm frame clamp, releasably attached to the frame; a clamp arm having a longitudinal dimension, releasably held and supported by the clamp arm frame clamp, and adjustable relative to the frame clamp along the longitudinal dimension; and a skull clamp, supported by the arm, and adapted to clamp onto the rim. Further included is at least one spatula arm subassembly, which has a spatula arm frame clamp, releasably attached to the frame; a spatula arm held and supported by the spatula arm frame clamp; and a spatula extending from the inward end of the spatula arm of the spatula arm subassembly.

13 Claims, 5 Drawing Sheets

(56) References Cited

U.S. PATENT DOCUMENTS

| | | | |
|---|---|---|---|
| 4,616,635 A * | 10/1986 | Caspar | A61B 17/02 600/215 |
| 5,284,129 A | 2/1994 | Agbodoe et al. | |
| 5,947,896 A | 9/1999 | Sherts et al. | |
| 7,232,411 B2 | 6/2007 | Dinkler, II et al. | |
| 7,435,219 B2 | 10/2008 | Kim | |
| 9,216,125 B2 | 12/2015 | Sklar | |
| 2001/0009971 A1 * | 7/2001 | Sherts | A61B 17/0293 600/231 |
| 2005/0080319 A1 * | 4/2005 | Dinkler, II | A61B 17/02 600/201 |
| 2006/0084843 A1 * | 4/2006 | Sommerich | A61B 17/02 600/210 |
| 2018/0042595 A1 * | 2/2018 | Tsubouchi | A61B 17/0206 |

FOREIGN PATENT DOCUMENTS

| | | |
|---|---|---|
| DE | 102010006575 A1 | 8/2011 |
| WO | 2003082123 A2 | 10/2003 |

* cited by examiner

APPARATUS AND METHOD FOR RETRACTING BRAIN TISSUE DURING BRAIN SURGERY

BACKGROUND

A brain surgeon performing surgery through an opening created in the skull, is typically faced with the challenge of pushing brain tissue out of the way of a target surgical location and restraining the brain tissue during surgery. In many surgical situations, this is done by finding a natural cleft between the lobes, working a pair of spatulas into the cleft and then separating the spatulas to separate the brain tissue. To keep the tissue separated as the surgeon operates, the spatulas must be held in place. This is typically done by arms that are attached to some article that is held in constant position, relative to the patient's head. Most typically, the arms are attached to the clamp that is used to stabilize the patients head during surgery, but in some cases the arms are attached to the surgical table. One disadvantage of these arrangements is that a long arm is necessary to reach from its mount. It is difficult to obtain the desired stability with such a long arm, and it may even obstruct the freedom of movement of the brain surgeon.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of an assembly for facilitating brain surgery performed through an opening having a rim, created in the skull of a patient and having a curved frame, defining an inward dimension and an outward dimension. Also, at least one clamp arm subassembly is attached to the frame, and has a clamp arm frame clamp, releasably attached to the frame; a clamp arm having a longitudinal dimension, releasably held and supported by the clamp arm frame clamp, and adjustable relative to the frame clamp along the longitudinal dimension; and a skull clamp, supported by the arm, and adapted to clamp onto the rim. Further included is at least one spatula arm subassembly, which has a spatula arm frame clamp, releasably attached to the frame; a spatula arm held and supported by the spatula arm frame clamp; and a spatula extending from the inward end of the spatula arm of the spatula arm subassembly.

In a second separate aspect, the present invention is a method of performing brain surgery on a patient having a skull and brain tissue, beginning with the creation of an opening, having a rim, in the skull. The method utilizes an assembly for facilitating brain surgery, which includes a curved frame, defining an inward dimension and an outward dimension; and a plurality of spatula arm subassemblies, each including a spatula arm frame clamp, releasably attached to the frame, a spatula arm held and supported by the spatula arm frame clamp and a spatula extending from the inward end of the spatula arm sub-assembly. In the method, this assembly is clamped to the rim and the spatula arms are positioned so that the spatulas engage the brain tissue in a manner that facilitates surgery.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Figure 1:
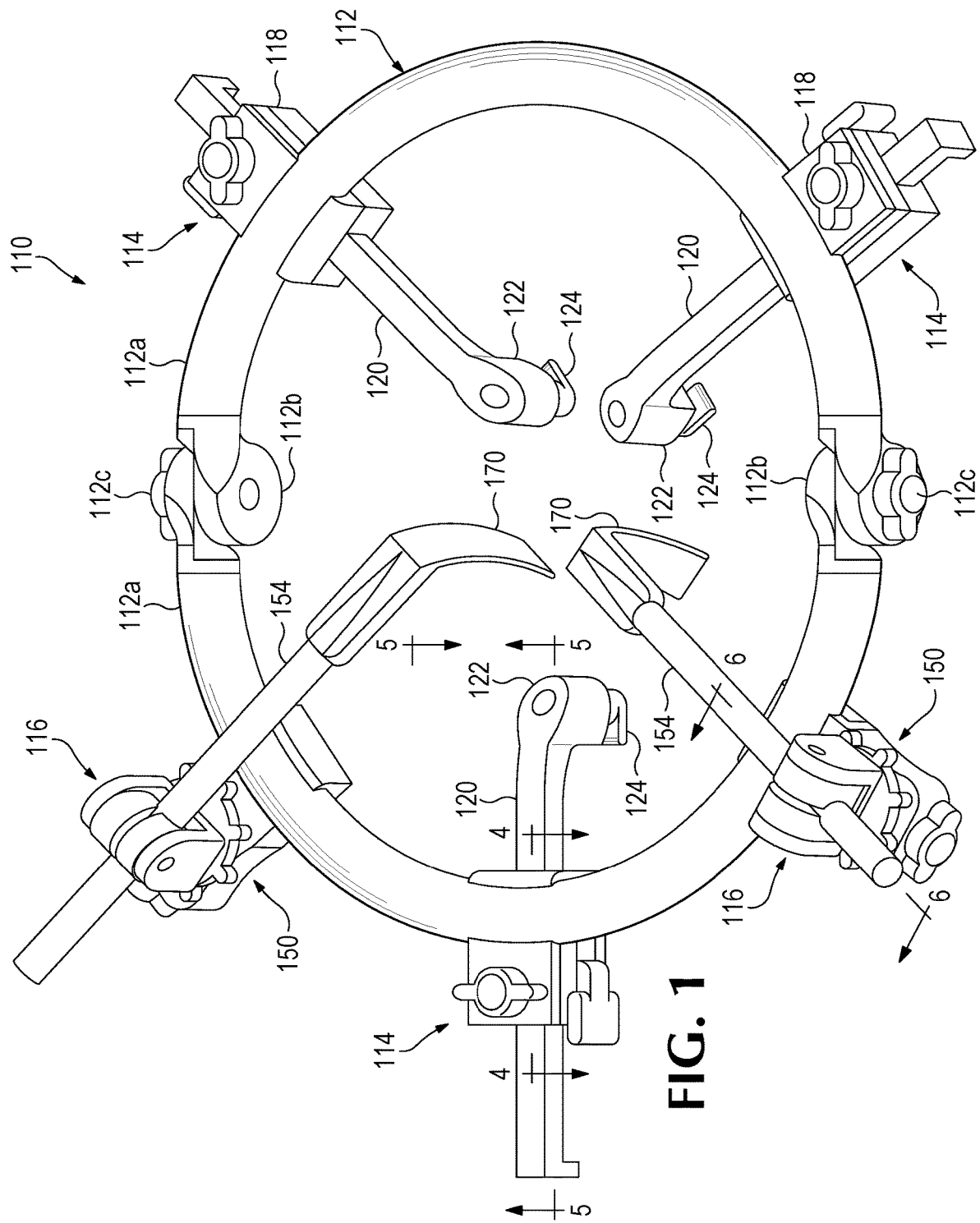
FIG. 1 shows an isometric view of a brain tissue retractor assembly, according to the present invention.

Referring to FIG. 1, in a first preferred embodiment, a brain tissue retraction assembly 110 takes the form of a hinged circular frame 112, having a set of releasably attached clamp arm sub-assemblies 114 and releasably attached spatula arm sub-assemblies 116. Frame 112 defines an interior or inner direction, meaning further to the interior of the frame, and an exterior or outer dimension, meaning away from the interior of the frame, or further outside of the frame. Frame 112 is divided into two semicircular pieces 112a, hinged together by a pair of hinges 112b, which can each be locked into position by a frame wing bolt 112c.

Figure 3:
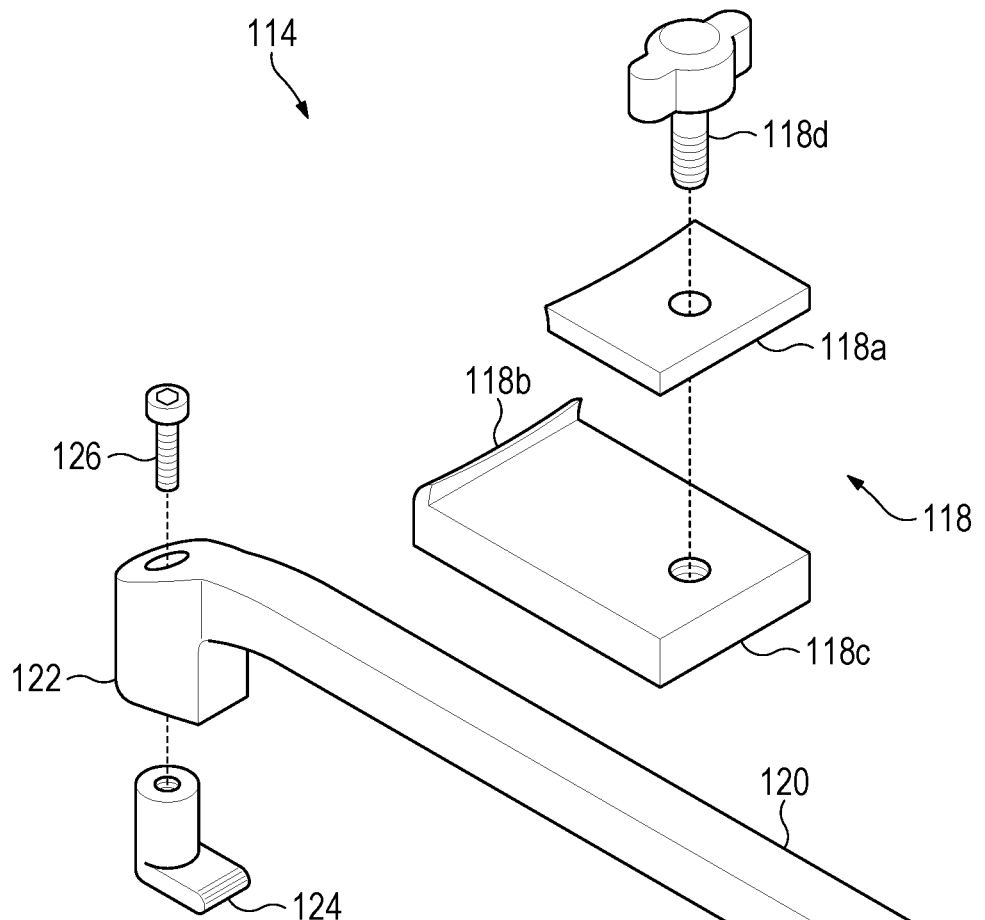
FIG. 3 shows an exploded perspective view of a skull clamp arm assembly, that forms a part of the brain tissue retractor assembly of FIG. 1.
Figure 3:
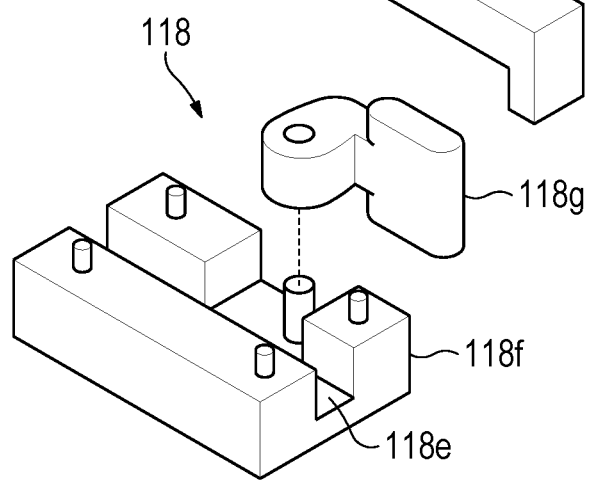
Figure 4:
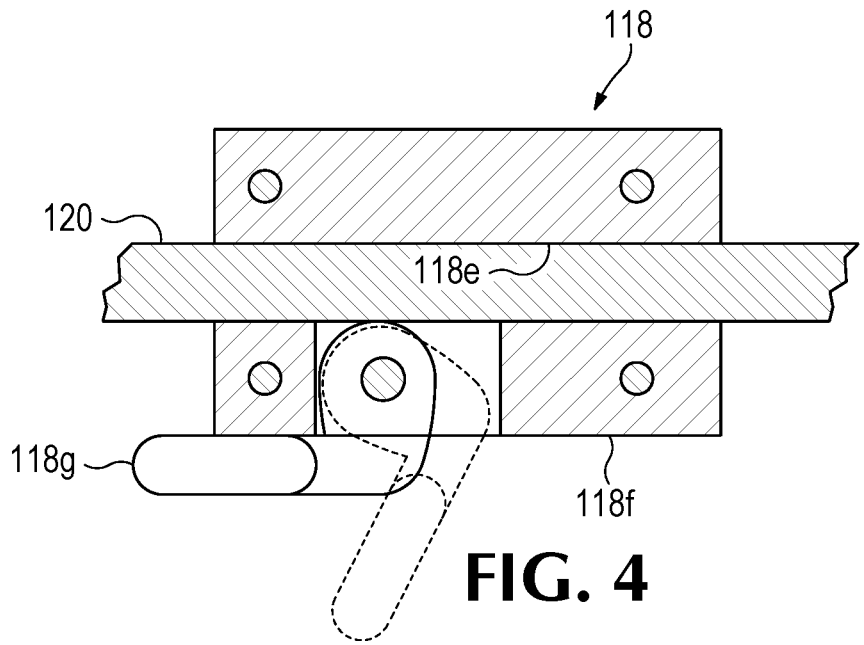
FIG. 4 shows a sectional view of a clamp arm lock, which forms a part of the skull clamp arm assembly of FIG. 3.
Figure 5:
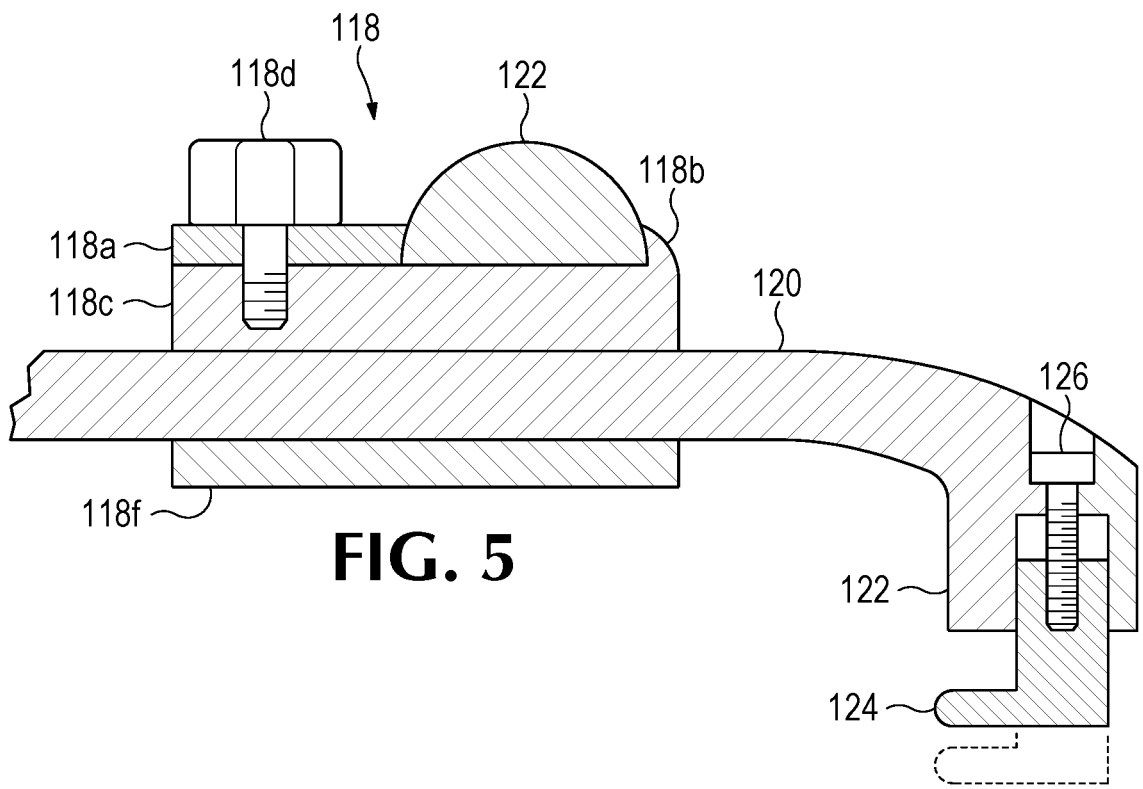
FIG. 5 shows a sectional view of a portion of the clamp arm assembly of FIG. 3, clamped to the frame of the brain tissue retractor assembly, of FIG. 1

Referring to FIGS. 3 and 5, each clamp arm sub-assembly 114 includes a clamp arm base 118, having a lock plate 118a that is opposed to a dog 118b, protruding up from a dog plate 118c. If a portion of frame 112 (FIG. 1) is interposed between plate 118a and dog 118b and a wing bolt 118d is tightened down, then frame 112 is held tightly between dog 118b and plate 118a. When wing bolt 118d is loosened, frame 112 is released from pressure and base 118 may be moved about frame 112 or removed entirely. A clamp arm 120 is slidingly engaged in a through-hole 118e in base block 118f and may be locked in place by locking lever 118g. In a preferred embodiment, frame 112 is semicircular in cross-section, so that the mutually opposed surfaces of member 118a and dog 118b fit conformally about from frame 112.

Figure 7:
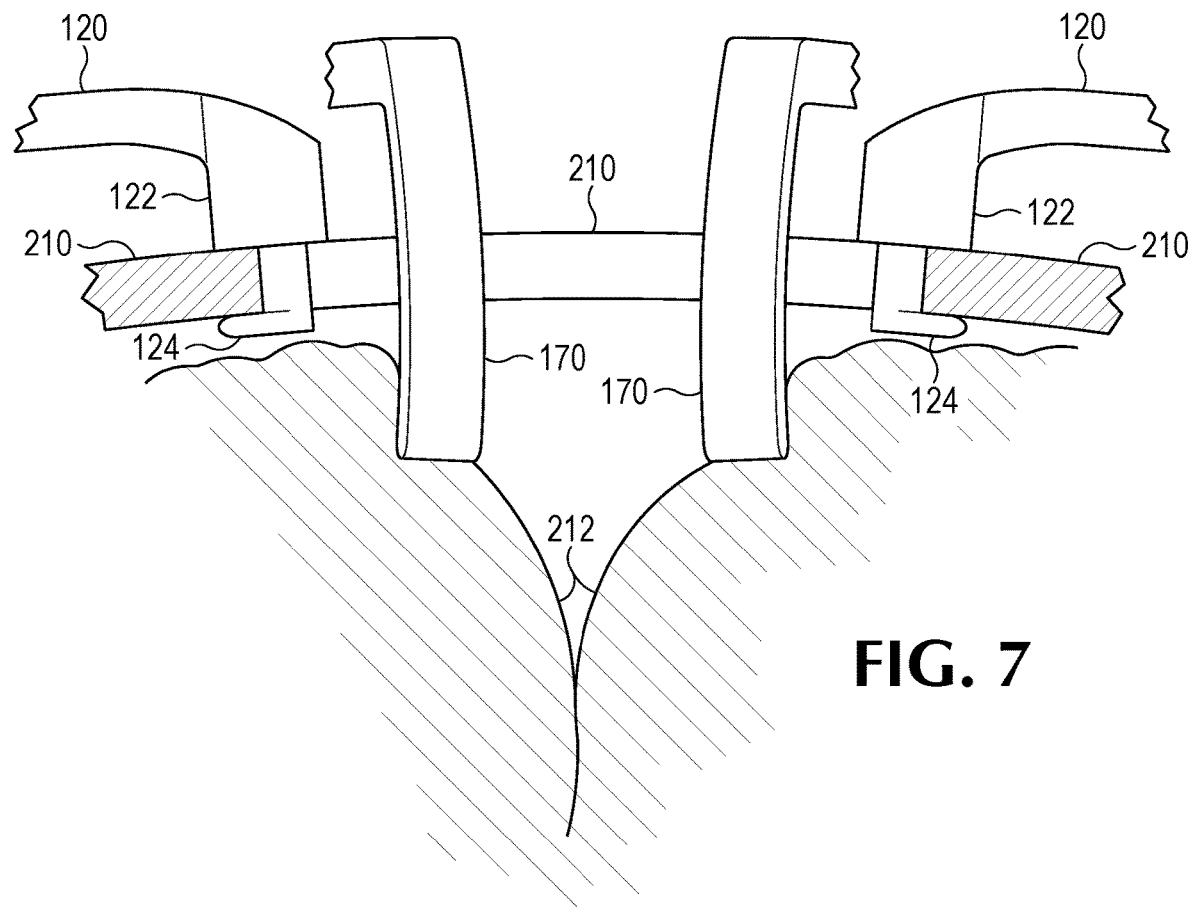
FIG. 7 is a detail partial sectional view of a portion of the brain tissue retractor assembly of FIG. 1, clamped to skull bone and spreading apart brain tissue.

Each clamp arm 120 terminates at its interior end in a clamp head 122, having a tongue 124 that is brought closer to clamp head 122 by a bolt 126, threaded through a hole in clamp head 122 and then helically engaged in a threaded hole in tongue 124, to tighten tongue 124 and clamp head 122 about the rim of a hole created in the skull, thereby holding frame 112 in place. Bolt 126 is loosened to loosen tongue 124 and head 122 from about the skull, to permit removal of the clamp head 122 and of the overall retraction assembly 110. Skilled persons will readily recognize that bolt 126, in cooperative engagement with tongue 124 and head 122 constitutes a tightening mechanism, and that as shown in FIGS. 3, 5 and 7, the top surface of tongue 124 and the opposed bottom surface of head 122 comprise mutually opposed parallel planar surfaces that can be brought together about rim 210 as shown in FIG. 7. Also, tongue 124 can be rotated relative to head 122, before being tightened into place by bolt 126. In one embodiment, the upper surface of tongue 124 and the lower surface of head 122 have a coating of a biocompatible and resiliently deformable material, such as silicone, to conform to the upper and lower surfaces of the skull hole rim. It is notable, however, that restraining brain tissue cannot apply a great force against the skull hole rim, as brain tissue is soft and pliable. Accordingly, every element of assembly 110 may be made of lightweight material and in thicknesses that do not provide the strength that might be necessary in other applications, but that are thin enough so that assembly 110 has a mass of, in one embodiment, less than 100 grams.

Figure 2:
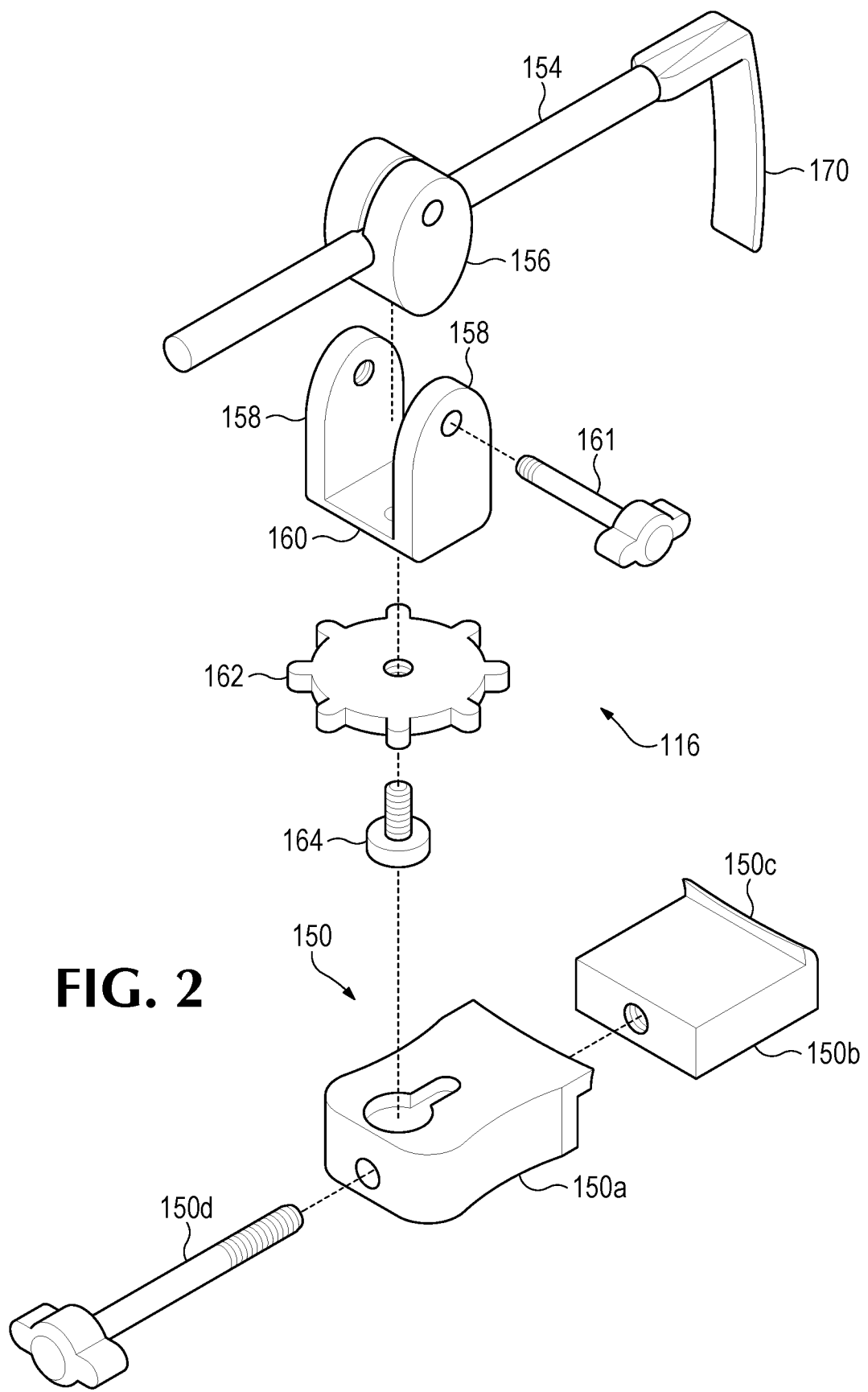
FIG. 2 shows an exploded perspective view of a spatula arm assembly, that forms a part of the brain tissue retractor assembly of FIG. 1.
Figure 6:
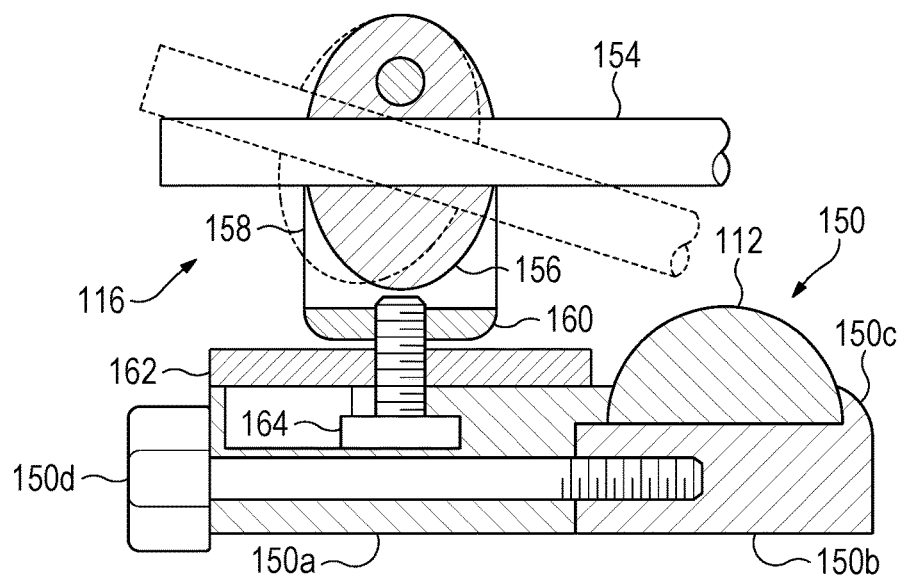
FIG. 6 is a detail sectional view of a portion of the spatula arm assembly of FIG. 2.

Referring to FIGS. 2 and 6, each spatula arm subassembly 116 includes a spatula-arm-base 150, including a base block 150a, and a clamping block 150b that includes an upwardly projecting dog 150c. A clamping wing bolt 150d is engaged into a threaded opening, which draws clamping block 150b towards base block 150a, when turned in a first direction, thereby clamping blocks 150a and 150b about frame 112. When wing bolt 150d is turned in the opposite direction, base 150 is loosened from frame 112, for movement along frame 112, or removal from frame 112. A spatula arm 154 is held in place between two vertically rotatably-ears 156, which are in turn held between two wings 158 of a mounting bracket 160. A locking wing bolt 162 is tightened to hold spatula arm 154 in place, so that it cannot be moved inwardly and outwardly, and to hold ears 156 in place by pressure from wings 158, so that ears 156 cannot be rotated vertically, which would thereby vertically rotate arm 154. In addition, bracket 160 is mounted to base 150 so that it can be horizontally rotated, thereby horizontally rotating arm 154. A locking ring 162 is rotatable and helically threaded engagement to a bolt 164, permitting ring 162 to be tightened down against base block 150a, thereby locking bracket 160, and thereby arm 154, in place against horizontal rotation. A spatula 170 extends downwardly at the end of arm 154.

In an alternative preferred embodiment, spatula arms that are deformable and that hold their shape after deformation are provided. These arms are deformed into position, holding spatulas to restrain the brain tissue.

Referring to FIGS. 1 and 7, to use assembly 110, clamp arm sub-assemblies 114 are moved on frame 112 and each clamp arm 120 is moved relative to its base 118, until clamp heads 122 are arranged about the rim 210 of a hole in the patient's skull, and sub-assemblies 114 and arms 120 are locked in place, and clamp heads 122 and tongues 124 are tightened about the rim 210, to hold assembly 110 in place. With spatula arms 154 in an upwardly tilting orientation, the spatula arm sub-assemblies 116 are arranged in placement on frame 112, so that spatulas 170 may be at a correct location and orientation when lowered into place. Spatula arms 154 are rotated horizontally so that each spatula 170 is oriented along a cleft in the brain tissue 212. Then (step not shown), while the brain tissue 212 is gently manually retracted, spatula arms 154 are vertically rotated down to place spatulas 170 so that they will continue to restrain the brain tissue 212 (as shown) when it is no longer manually restrained. Spatulas 170, in one embodiment, are made of a thin sheet of metal, that is resiliently deformable. Other materials may also be used.

In one preferred embodiment, frame 112 is 18 cm (7 in) across at the hinges, and 16 cm (6.5 in) across in the orthogonal dimension. The frame 112 defines an interior round area, having a diameter of about 15.24 cm (6 in.), for an interior area of about 730 cm. In a preferred embodiment, frame 112 is made of stainless steel, as are the sub-assemblies.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. An assembly for facilitating brain surgery performed through an opening having a rim, created in the skull of a patient, comprising:
   (a) a curved frame, defining an inward dimension and an outward dimension;
   (b) at least one clamp arm sub-assembly, attached to said frame, including:
      (i) a clamp arm frame clamp, releasably attached to said frame;
      (ii) a clamp arm having a longitudinal dimension, releasably held and supported by said clamp arm frame clamp, and adjustable in position relative to said frame clamp along said longitudinal dimension;
      (iii) a skull clamp, supported by said arm, and having a head and a tongue, which have mutually opposed parallel planar surfaces, and a tightening mechanism permitting said tongue to be brought closer to said head from an initial position, to clamp said rim between said mutually opposed parallel planar surfaces of said head and said tongue;
   (c) at least one spatula arm sub-assembly, including:
      (i) a spatula arm frame clamp, releasably attached to said frame;
      (ii) a spatula arm held and supported by said spatula arm frame clamp, and extending in said inward dimension to an inward end; and
      (iii) a spatula extending from said inward end of said spatula arm of said spatula arm sub-assembly.

2. The assembly of claim 1, wherein said frame forms a closed form.

3. The assembly of claim 2, wherein said frame is an ellipsoid.

4. The assembly of claim 1, wherein said frame comprises a first curved portion and a second curved portion, hinged together, whereby said second curved portion may be placed into a different orientation than said first curved portion.

5. The assembly of claim 1, further comprising additional clamp arm sub-assemblies, available for attachment to said frame.

6. The assembly of claim 1, further comprising additional spatula arm sub-assemblies, available for attachment to said frame.

7. The assembly of claim 1, wherein said spatula arm is rigid and has a longitudinal dimension and said spatula arm frame clamp permits adjustment of said position of said spatula arm along its longitudinal axis, relative to said spatula arm frame clamp and further permits horizontal and vertical rotation of said spatula arm to permit said spatula to be vertically rotated into position in brain tissue at a beneficial orientation.

8. The assembly of claim 7, further wherein said spatula arm assembly includes locking mechanisms, permitting said spatula arm to be locked into place at a beneficial position and orientation.

9. The assembly of claim 1, wherein said spatula arm is flexible, permitting it to be bent into a preferred shape, and wherein it holds this shape afterwards.

10. The assembly of claim 1, wherein said head defines a through hole, and wherein a bolt is engaged to said through hole and with said tongue, thereby forming said tightening mechanism, and so that when said bolt is tightened said tongue is lifted toward said head, thereby clamping any interposed element between said tongue and said head, and wherein said tongue can be brought into close enough proximity to said bottom surface that a thickness of human skull can be clamped between said tongue and said bottom surface.

11. The assembly of claim 10, wherein said mutually opposed parallel planar surfaces are both coated in resiliently deformable, biocompatible material.

12. The assembly of claim 11, wherein said material is silicone.

13. The assembly of claim 1, wherein said tongue is horizontally rotatable, relative to said head.

* * * * *